(12) United States Patent
Yamashita et al.

(10) Patent No.: US 9,220,643 B2
(45) Date of Patent: Dec. 29, 2015

(54) DISPOSABLE WEARING ARTICLE WITH ELASTIC BANDS

(75) Inventors: Mariko Yamashita, Kanonji (JP); Toshifumi Otsubo, Kanonji (JP); Tatsuya Hashimoto, Kanonji (JP); Shinichi Ishikawa, Kanonji (JP); Jun Okuda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 1012 days.

(21) Appl. No.: 13/260,827

(22) PCT Filed: Mar. 30, 2010

(86) PCT No.: PCT/JP2010/002334
§ 371 (c)(1),
(2), (4) Date: Sep. 28, 2011

(87) PCT Pub. No.: WO2010/113488
PCT Pub. Date: Oct. 7, 2010

(65) Prior Publication Data
US 2012/0029460 A1   Feb. 2, 2012

(30) Foreign Application Priority Data

Mar. 30, 2009   (JP) ................................. 2009-080821
Mar. 24, 2010   (JP) ................................. 2010-068328

(51) Int. Cl.
*A61F 13/15*   (2006.01)
*A61F 13/20*   (2006.01)
*A61F 13/49*   (2006.01)

(52) U.S. Cl.
CPC ..... *A61F 13/49017* (2013.01); *A61F 13/15593* (2013.01); *A61F 13/4902* (2013.01); *A61F 13/49011* (2013.01)

(58) Field of Classification Search
CPC .................. A61F 13/49017; A61F 13/49011; A61F 13/49019; A61F 13/4902; A61F 2013/530167; A61F 13/15593
USPC .......................... 604/385.01, 385.24, 385.27
See application file for complete search history.

(56) References Cited

U.S. PATENT DOCUMENTS

| | | | |
|---|---|---|---|
| 5,576,090 A | | 11/1996 | Suzuki |
| 5,576,091 A | * | 11/1996 | Zajaczkowski et al. ...... 428/192 |
| 5,807,368 A | * | 9/1998 | Helmer .......................... 604/373 |
| 7,442,188 B2 | * | 10/2008 | Franklin et al. ........... 604/385.23 |

(Continued)

FOREIGN PATENT DOCUMENTS

| | | |
|---|---|---|
| EP | 0788874 A1 | 8/1997 |
| JP | 62-243806 A | 10/1987 |

(Continued)

OTHER PUBLICATIONS

Supplementary European Search Report issued Nov. 26, 2013, corresponds to European patent application No. 10758268.6.

(Continued)

*Primary Examiner* — Michele M Kidwell
(74) *Attorney, Agent, or Firm* — Hauptman Ham, LLP

(57) ABSTRACT

A disposable wearing article includes, in an elastic region in a periphery of at least a waist- or leg-opening, an elastic band formed of a fibrous non-woven fabric which is elastically contractible and has a plurality of first gathers extending in a length direction so as to undulate in a width direction thereof.

11 Claims, 8 Drawing Sheets

(56) References Cited

U.S. PATENT DOCUMENTS

2002/0151863 A1  10/2002  Toyoshima
2006/0270302 A1* 11/2006  Ando et al. .................. 442/328

FOREIGN PATENT DOCUMENTS

| JP | 5-228177 A | 9/1993 |
| JP | 07-308341 A | 11/1995 |
| JP | 10-000712 A | 1/1998 |
| JP | 2002-291797 A | 10/2002 |
| JP | 2008173285 A | 7/2008 |
| WO | 94/28845 * 12/1994 | .............. A61F 13/15 |

OTHER PUBLICATIONS

International Search Report for PCT/JP2010/002334 mailed Jul. 13, 2010.

* cited by examiner

DISPOSABLE WEARING ARTICLE WITH ELASTIC BANDS

RELATED APPLICATIONS

The present application is a National Phase of International Application Number PCT/JP2010/002334, filed Mar. 30, 2010 and claims priority from, Japanese Application Numbers 2009-080821, filed Mar. 30, 2009 and 2010-068328, filed Mar. 24, 2010.

TECHNICAL FIELD

The present disclosure relates to a disposable wearing article and more specifically to a wearing article such as a disposable diaper having elastic regions defined by elastic bands.

BACKGROUND

It has been known to attach elastic bands to wearing articles such as disposable diapers along peripheries of waist-openings and/or leg-openings to define elastic regions along these peripheries.

In the disposable absorbent pants disclosed, for example, by JP 62-243806 A (PATENT REFERENCE 1), elastic members made of, for example, urethane foam (Spandex), each having the width in a range of 10 to 45 mm, are bonded to the respective peripheries of the waist-opening and the leg-openings to form these peripheries with the elastic regions including gathers. The elastic members extend straight in the transverse direction of the pants along the periphery of the waist-opening. However, along the periphery of each leg-opening, some of the elastic members extend straight in the transverse direction of the pants while other elastic members extend straight in the vertical direction of the pants.

In the disposable diaper disclosed by JP 07-308341 A (PATENT REFERENCE 2), leg-surrounding gasket-cuffs are formed with curved elastic regions. These elastic regions are obtained by bonding belt-like elastic sheet members evenly stretched in the length direction to the respective gasket-cuffs so that the regions along which the elastic sheet members are bonded to the gasket-cuffs may describe curved lines. The elastic sheet members are integrated with the gasket-cuffs to define the elastic regions around the wearer's legs. Polyurethane foam (Spandex), polyethylene foam or the like are used as material for the elastic sheet members.

In both of the known articles using belt-like elastic members to define elastic regions, the preferred belt-like elastic members are made of urethane foam (Spandex). The belt-like elastic members made of such material are elastically deformable in a recoverable manner as these elastic members are compressed in the thickness direction and whereby render the peripheries of the waist- and/or leg-openings comprising such elastic members soft and comfortably textured. The known wearing articles also use, in addition to urethane foam, plastic film, thin layered sheet of natural rubber, synthetic rubber or the like, and melt blown non-woven fabric as the material for the belt-like elastic members. However, it is often difficult for an elastic member made of plastic film, thin layered sheet of rubber or non-woven fabric to be as elastically recoverable as an elastic member made of polyurethane foam. Consequently, it is difficult for elastic members made of such plastic films, thin layered sheets of rubber or non-woven fabrics to render the peripheries of the waist- and/or leg-openings soft and comfortably textured.

There is a need to provide waist- and/or leg-openings with soft and comfortably textured peripheries even when these peripheries are elasticized by elastic members made of elastically contractible non-woven fabric.

CITATION LIST

Patent Literature

[PTL 1]
Japanese Patent Application Laid-Open Publication No. 62-243806 A
[PTL 2]
Japanese Patent Application Laid-Open Publication No. 07-308341 A

SUMMARY

One or more embodiments of the invention relates to a disposable wearing article having front and rear waist regions, a crotch region between the front and rear waist regions, a waist-opening defined by the front and rear waist-regions, and leg-openings defined by the front and rear waist regions and the crotch region. A periphery of at least one of the waist-opening and the leg-openings has an elastic region including an elastic band of a first fibrous sheet which is elastically contractible in a circumferential direction of the at least one of the waist-opening and the leg-openings.

In this article, the elastic band includes a plurality of first gathers which extend in a length direction of the elastic band along the circumferential direction and undulate in a width direction of the elastic band.

Preferably, the front and rear waist regions include an inner sheet and an outer sheet, at least one of both surfaces of the elastic band is bonded to at least one of the inner and outer sheets so as to form second gathers which extend in a direction crossing the first gathers are formed, when the elastic band contracts.

DETAILED DESCRIPTION

Details of a disposable wearing article according to exemplary embodiments of the present invention will be more fully understood from the description given hereunder with reference to the accompanying drawings.

Figure 1:
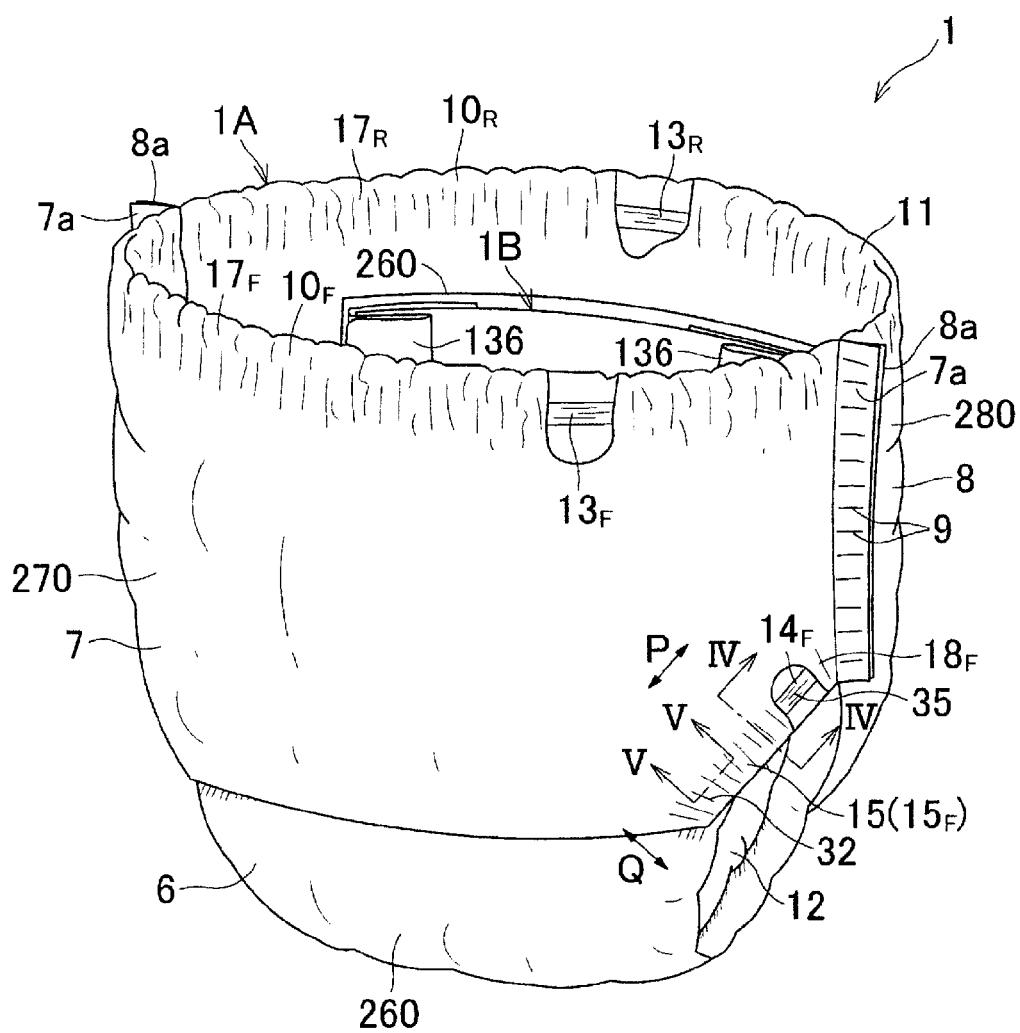
FIG. 1 is a partially cutaway perspective view of a pant-type diaper in accordance with one or more embodiments.

FIG. 1 is a partially cutaway perspective view of a pant-type diaper 1 which is a typical example of a disposable wearing article according to one or more embodiments of the present invention, wherein a transverse direction, a front-back direction and a vertical direction are respectively designated by arrows X, Y and Z. The diaper 1 comprises a pant-shaped chassis 1A and a bodily fluid absorbent structure 1B attached to the inner side thereof. The chassis 1A comprises, in turn, a crotch region 6, a front waist region 7 extending forward from the crotch region 6 and a rear waist region 8 extending rearward from the crotch region 6. The front and rear waist regions 7, 8 are put flat together along opposite side edges 7a, 8a of the respective waist regions 7, 8 and joined to each other at a plurality of joints 9 arranged intermittently in the vertical direction Z along the respective side edges 7a, 8a. Thereupon, these front and rear waist regions 7, 8 cooperate with each other to define a waist-opening 11 of the diaper 1 and, at the same time, the front and rear waist regions 7, 8 cooperate with the crotch region 6 to define a pair of leg-openings 12. The chassis 1A further includes a front panel 270 defining the entirety of the front waist region 7 plus a portion of the front half of the crotch region 6. The chassis 1A also includes a rear panel 280 defining the entirety of the rear waist region 8 plus a portion of the rear half of the crotch region 6. The front panel 270 is provided with a front waist elastic band $13_F$ extending in the circumferential direction of the waist-opening 11 along a peripheral edge $10_F$ of the waist-opening 11, and front leg elastic bands $14_F$ extending in the circumferential direction of the leg-openings 12 along respective front peripheral edges $15_F$. These elastic bands $13_F$, $14_F$ are attached under tension to the front panel 270 so as to define a front waist elastic region $17_F$ and front leg elastic regions $18_F$. The rear panel 280 is provided with a rear waist elastic band $13_R$ extending in the circumferential direction of the waist-opening 11 along a peripheral edge $10_R$ of the waist-opening 11, and rear leg elastic bands $14_R$ extending in the circumferential direction of the leg-openings 12 along respective rear peripheral edges $15_R$. These elastic bands $13_R$, $14_R$ are attached under tension to the rear panel 280 so as to define a rear waist elastic region $17_R$ and rear leg elastic regions $18_R$ (See FIG. 2). It should be appreciated that, in the diaper 1 shown in FIG. 1, these elastic regions $17_F$, $17_R$, $18_F$, $18_R$ are in contracted states.

The wording "band" in this embodiment refers to a member which is formed of sheet material and a width dimension of the member is larger than that of a thickness dimension thereof and a length dimension thereof is larger than the width dimension.

Figure 2:
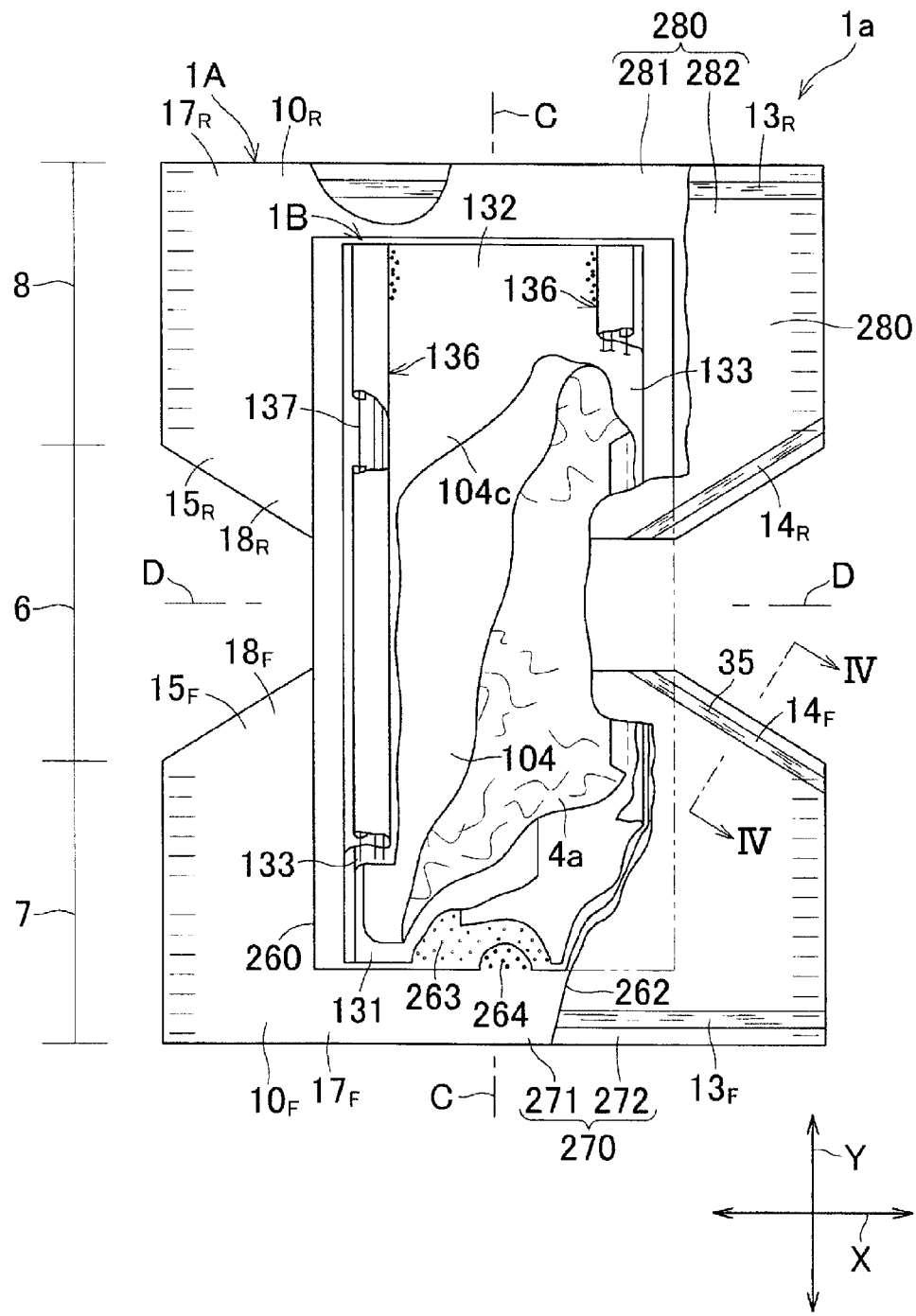
FIG. 2 is a partially cutaway plan view showing the diaper of FIG. 1 in a flatly developed state.
Figure 3:
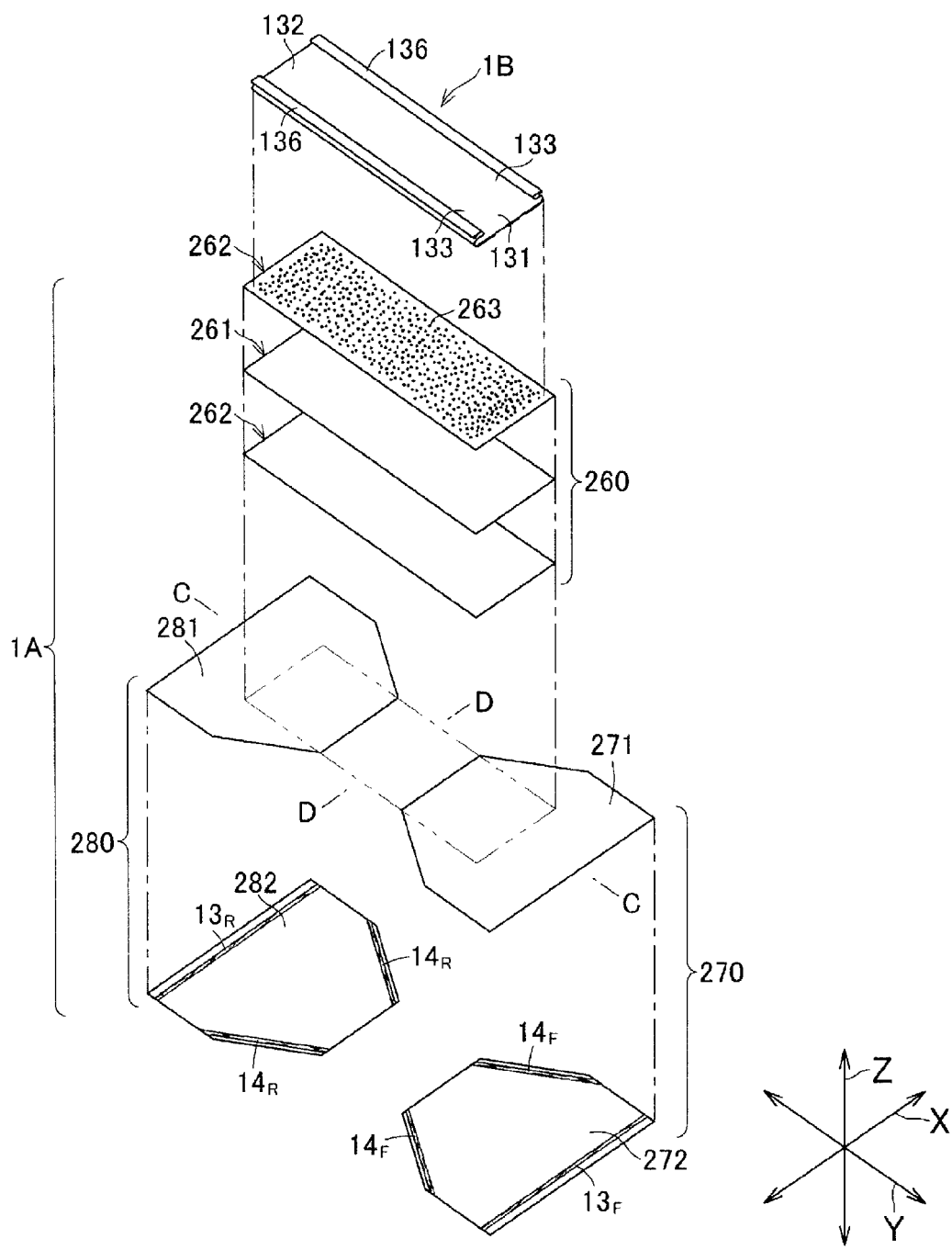
FIG. 3 is an exploded perspective view of the flatly developed diaper.

FIG. 2 is a partially cutaway plan view of a developed diaper 1a obtained by disjoining the front and rear waist regions 7, 8 from each other along the arrays of the joints 9 and flatly developing the crotch region 6 and the front and rear waist regions 7, 8 in the transverse direction X as well as in the front-back direction Y. FIG. 3 is an exploded perspective view of this flatly developed diaper 1a. In FIGS. 2 and 3, C-C is the longitudinal center line extending in the front-back direction Y to bisect a width of the flatly developed diaper 1a in the transverse direction X, and D-D is the transverse center line extending orthogonally to the longitudinal center line C-C to bisect a length of the flatly developed diaper 1a in the front-back direction Y. The shape of the developed diaper 1a is symmetric about the longitudinal center line C-C.

Referring to FIGS. 2 and 3, the chassis 1A has the front panel 270 (of a substantially hexagonal shape in the particularly illustrated configuration) formed of a fibrous sheet, preferably a fibrous non-woven fabric defining the front waist region 7 and a part of the crotch region 6, the rear panel 280 (of a substantially hexagonal shape in the particularly illustrated configuration) formed of a fibrous sheet, preferably a fibrous non-woven fabric defining the rear waist region 8 and a part of the crotch region 6, and a middle panel 260 (of a substantially rectangular shape in the particularly illustrated configuration) defining apart of the crotch region 6. The front panel 270 comprises sheet members including an inner sheet 271 and an outer sheet 272 which, in the particularly illustrated configuration, are identical in shape as well as in size and are bonded together by hot melt adhesive (not shown). A single front waist elastic band $13_F$ and a pair of front leg elastic bands $14_F$ opposed in the transverse direction X are sandwiched between these inner and outer sheets 271, 272 and bonded under tension to these inner and outer sheets 271, 272 by hot melt adhesive (not shown). The inner sheet 271, the front waist elastic band $13_F$ and the outer sheet 272 cooperate one with another to define a front waist elastic region $17_F$, while the inner sheet 271, the front leg elastic bands $14_F$ and the outer sheet 272 cooperate one with another to define a front leg elastic region $18_F$ for each leg opening 12. The rear panel 280 comprises sheet members including an inner sheet 281 and an outer sheet 282 which, in the particularly illustrated configuration, are identical to each other in shape as well as in size and are bonded together by hot melt adhesive (not shown). A single rear waist elastic band $13_R$ and a pair of rear leg elastic bands $14_R$ opposed in the transverse direction X are sandwiched between these inner and outer sheets 281, 282 and bonded under tension to these inner and outer sheets 281, 282 by hot melt adhesive (not shown). The inner sheet 281, the rear waist elastic band $13_R$ and the outer sheet 282 cooperate one with another to define a rear waist elastic region $17_R$, while the inner sheet 281, the rear leg elastic bands $14_R$ and the outer sheet 282 cooperate one with another to define a rear leg elastic region $18_R$ for each leg opening 12. The middle panel 260 comprises a leakage-barrier plastic film 261 and a pair of cover sheets 262 sandwiching therebetween the leakage-barrier plastic film 261, wherein these plastic film 261 and cover sheets 262 are put flat and bonded together by hot melt adhesive (not shown). The leakage-barrier plastic film 261 is, in some embodiments, formed of a liquid-impervious plastic film and each cover sheet 262 is, in some embodiments, formed of a fibrous sheet, preferably a fibrous non-woven fabric. Such middle panel 260 has front and rear ends respectively extending to respective inner sides (i.e., respective upper sides as viewed in FIG. 3) of the front and rear panels 270, 280 and bonded to the inner sides by hot melt adhesive 264 (See FIG. 2) so as to connect the front panel 270 with the rear panel 280 and obtain the chassis 1A. To the inner side of the middle panel 260, the bodily fluid absorbent structure 1B is bonded by hot melt adhesive 263 coated on this inner side.

As will be apparent from FIG. 2, the bodily fluid absorbent structure 1B, in the particularly illustrated configuration, has a rectangular shape which is elongated in the front-back direction Y and contoured by a pair of opposite side edges 133 extending parallel to the longitudinal center line C-C, and front and rear ends 131, 132 extending parallel to the transverse center line D-D. The side edges 133 are respectively formed with leakage-barrier cuffs 136. In such bodily fluid absorbent structure 1B, an assembly of bodily fluid absorbent material 4a, such as fluff pulp and/or super-absorbent polymer particles, is wrapped with tissue paper 104, and the side of this wrapped assembly facing the wearer's skin is covered with a liquid-pervious skin-contact sheet 104c (see FIG. 1). The leakage-barrier cuffs 136 are, in some embodiments, formed of a liquid-impervious sheet. The bodily fluid absorbent structure 1B is provided with the leakage-barrier cuffs 136 and, in addition, indirectly lined with the leakage-barrier plastic film 261 in the middle panel 260. In this way, the leakage-barrier capability of the bodily fluid absorbent structure 1B is correspondingly improved. In other embodiments (not shown) of the present invention, a diaper without leakage-battier cuffs is provided.

In each leakage-barrier cuff 136, a plurality of rubber strings 137 extending in the front-back direction Y as viewed in FIG. 2 are bonded under tension to the liquid-impervious sheet defining the leak-proof barrier 6 by hot melt adhesive (not shown). Referring to FIGS. 2 and 3, while the liquid-impervious sheet is shown to be folded in a Z- or in an inverted Z-shape as viewed in the transverse direction X, the leakage-barrier cuffs 136 in the pant-type diaper 1 can rise up, as shown in FIG. 1, on the inner side of the skin-contact sheet 104c along the respective side edges 133 of the bodily fluid absorbent structure 1B as the rubber strings 137 contract.

Figure 4:
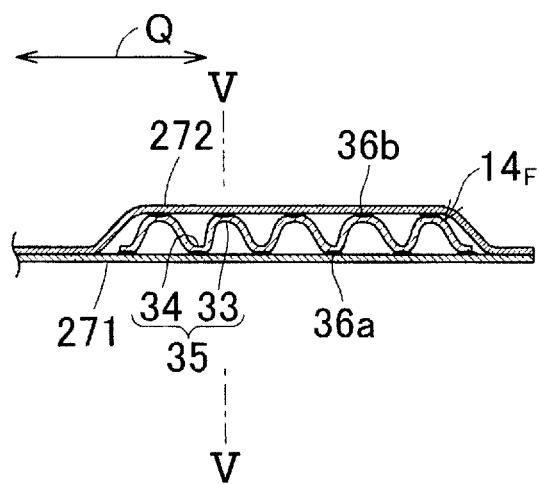
FIG. 4 is a sectional view taken along the line IV-IV in FIG. 1.

FIG. 4 is a sectional view taken along the line IV-IV in FIG. 1. While the position of the line IV-IV is indicated in FIG. 2 also, it should be appreciated that the front leg elastic band $14_F$ in FIG. 2 is not in a contracted state as seen in FIGS. 1 and 4, but in a stretched state. Referring to FIG. 1, the front periphery $15_F$ of each leg-opening 12 defined by the front panel 270 is formed with a plurality of second gathers 32 extending to intersect with a circumferential direction P of the leg opening 12 (see FIG. 5). These second gathers 32 are formed in the inner and outer sheets 271, 272 in the front panel 270 as the front leg elastic band $14_F$ contracts in the circumferential direction P. The front leg elastic band $14_F$ extends in the circumferential direction P and is formed, in the contracted state shown in FIG. 4, with crests 33 and troughs alternating in a direction intersecting with the circumferential direction P (i.e., in a width direction Q of the elastic band $14_F$) to form first gathers 35 longitudinally extending between opposite ends of the front leg elastic band $14_F$ in the circumferential direction P. The inner sheet 271 is bonded to the troughs 34 of the front leg elastic band $14_F$ by hot melt adhesive 36a and the outer sheet 272 is bonded to the crests 33 of the front leg elastic band $14_F$ by hot melt adhesive 36b. More specifically, these inner and outer sheets 271, 272 are bonded to the front leg elastic band $14_F$ intermittently in the circumferential direction P, i.e., in the length direction as well as in the width direction Q of the front leg elastic band $14_F$. The inner and outer sheets 271, 272 are flat and adhesive-bonded or fusion-bonded together outside the front leg elastic band $14_F$ in the width direction Q of the elastic band $14_F$.

Figure 5:
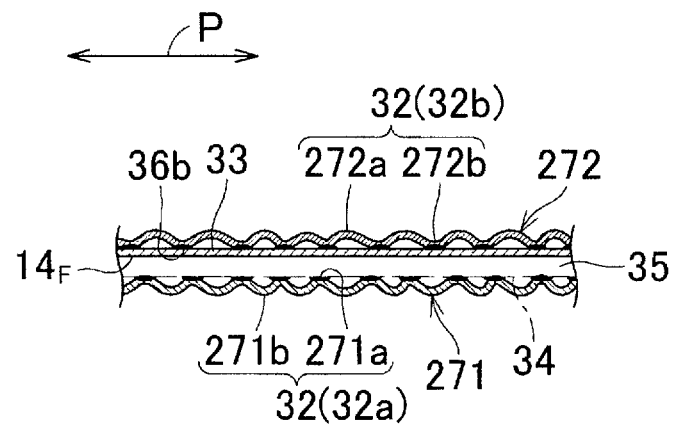
FIG. 5 is a sectional view taken along the line V-V in FIG. 1.

FIG. 5 is a sectional view taken along the line V-V in FIG. 1 and the position of this line V-V is indicated in FIG. 4 also. In FIG. 5, the crests 33 in the front leg elastic band $14_F$ are indicated by solid lines and the troughs 34 are indicated by imaginary lines. The inner and outer sheets 271, 272 in the front panel 270 are formed with second gathers 32 with alternating crests and troughs in the circumferential direction P. Unlike the first gathers 35 which are elongated in the length direction of the elastic band, i.e., the circumferential direction P, the second gathers 32 are elongated in the width direction Q of the elastic band $14_F$ as best seen in FIG. 1. Second gathers 32a constituting the second gathers 32 formed in the inner sheet 271 comprise crests 271a and troughs 271b, while second gathers 32b constituting the second gathers 32 formed in the outer sheet 272 comprise crests 272a and troughs 272b.

In the front panel 270 including the front peripheries $15_F$ of the respective leg-openings 12, the inner and outer sheets 271, 272 are, in some embodiments, formed, for example, of (i) a spunbonded fibrous non-woven fabric, (ii) a melt blown fibrous non-woven fabric or (iii) a laminate of a spunbonded fibrous non-woven fabric, a melt blown fibrous non-woven fabric and a spunbonded fibrous non-woven fabric. Such laminate is referred to also as an SMS fibrous non-woven fabric. Each of the inner and outer sheets 271, 272 has a basis mass of about 10 to about 100 g/m². The front leg elastic bands $14_F$ are formed, in some embodiments, of an elastically stretchable and contractible fibrous non-woven fabric or an elastically stretchable and contractible plastic film. In a preferred configuration, the front leg elastic bands $14_F$ are formed of (1) an elastic fibrous non-woven fabric made of elastic fibers, such as urethane elastic fibers, or (2) an elastic fibrous non-woven fabric made of elastic fibers mixed with non-elastic thermoplastic synthetic fibers. The front leg elastic bands $14_F$ have a basis mass of about 20 to about 100 g/m². The preferred configuration of the front leg elastic band $14_F$ has a width of at least about 10 mm, preferably about 10 to about 40 mm and includes 3 to 7 crests 33 or troughs 34 per unit width of about 10 mm alternating in the width direction Q. The height of the crests 33 depends on the thickness of the elastic fibrous non-woven fabric forming the front leg elastic band $14_F$ and, for the fibrous non-woven fabric thickness of about 1 to about 2 mm, the height of the crests 33 is, in some embodiments, in a range of 1.2 to 3 times this thickness. Measurements of the height of the crests and the thickness of the fibrous non-woven fabric in this disclosure are carried out by subjecting the test pieces to a compression force of 0.5 g/cm² using Automatic Compression Tester KES-FB3-AUTO-A (manufactured by KATO TECH CO. LTD. in Japan) as measuring means.

The front waist elastic band $13_F$, in a preferred configuration, has a width of at least about 10 mm, preferably about 10 to about 40 mm and a plurality of gathers longitudinally extending in the length direction of the elastic band (i.e., in the circumferential direction of the waist opening 11) as in the case of the front leg elastic bands $14_F$. In some embodiments, a plurality of rubber strings each having a diameter or a width of about 0.3 to about 3 mm are used instead of the front waist elastic band $13_F$.

In the front panel 270, the front waist elastic band $13_F$ and the front leg elastic bands $14_F$ are bonded to the inner and outer sheets under appropriate tension, for example, under a longitudinal elongation extension of 1.5 to 4 times the length of the elastic bands in the relaxed state. "Relaxed state" is used herein to mean a state of an elastic component such as the elastic bands $13_F$, $13_R$, $14_F$, $14_R$ and the elastic fibrous non-woven fabric web 501 (see FIGS. 6-8) to be incorporated into a disposable wearing article in accordance with embodiments when the elastic component is relaxed without being bonded to any other material and subject to any external force.

Along the front periphery $15_F$ of the diaper's leg-opening 12 constructed in this manner, the first gathers 35 comprising the crests 33 and the troughs 34 of the front leg elastic band $14_F$, the second gathers 32a defined by the crests 271a and the troughs 271b of the inner sheet 271, and the second gathers 32b defined by the crests 272a and the troughs 272b of the outer sheet 272 are placed one upon another to provide the bulky, soft and comfortably textured front periphery $15_F$. In addition, the initial state of the front periphery $15_F$ can be rapidly elastically restored after the front periphery $15_F$ has been compressed in the thickness direction. The reason is that the front leg elastic band $14_F$ is formed of the elastically stretchable and contractible fibrous non-woven fabric or plastic film. While the second gathers 32 in the inner and outer sheets 217, 272 tend to disappear as the front periphery $15_F$ in FIG. 1 is stretched in the circumferential direction P, the first gathers 35 in the front leg elastic band $14_F$ undulating in the width direction Q do not disappear and, consequently, the front periphery $15_F$ remains bulky, soft and elastically deformable in the thickness direction even when it is in a stretched state. With the diaper 1 put on the wearer's body, the front periphery $15_F$ easily bend along the first gathers 35 toward the exterior of the diaper 1 in accordance with a movement of the leg of the wearer and thereby so as not to prevent the movement.

In the exemplarily illustrated diaper 1, the leg elastic band $14_R$ in the rear panel 280 may be formed with gathers undulating in the transverse direction thereof and extending in the circumferential direction as in the case of the front leg elastic band $14_F$ to assure that the periphery $15_R$ of the leg-opening 12 in the rear panel 280 also functions in the same manner as the periphery $15_F$ functions. One or both of the front waist elastic band $13_F$ and the rear waist elastic band $13_R$ may be formed with gathers undulating in the width direction thereof as in the case of the front leg elastic band $14_F$ to obtain soft and comfortably textured periphery 10 of the waist-opening 11. In some embodiments, a plurality of rubber strings is used in place of at least one of the front and rear waist elastic bands $13_F$, $13_R$. It is within the scope of this disclosure to make at least one of the front and/or rear periphery 10 of the waist-opening 11 and/or the respective peripheries $15_R$ and/or $15_F$ of each or both leg-openings 12 soft and comfortably textured.

Figure 6:
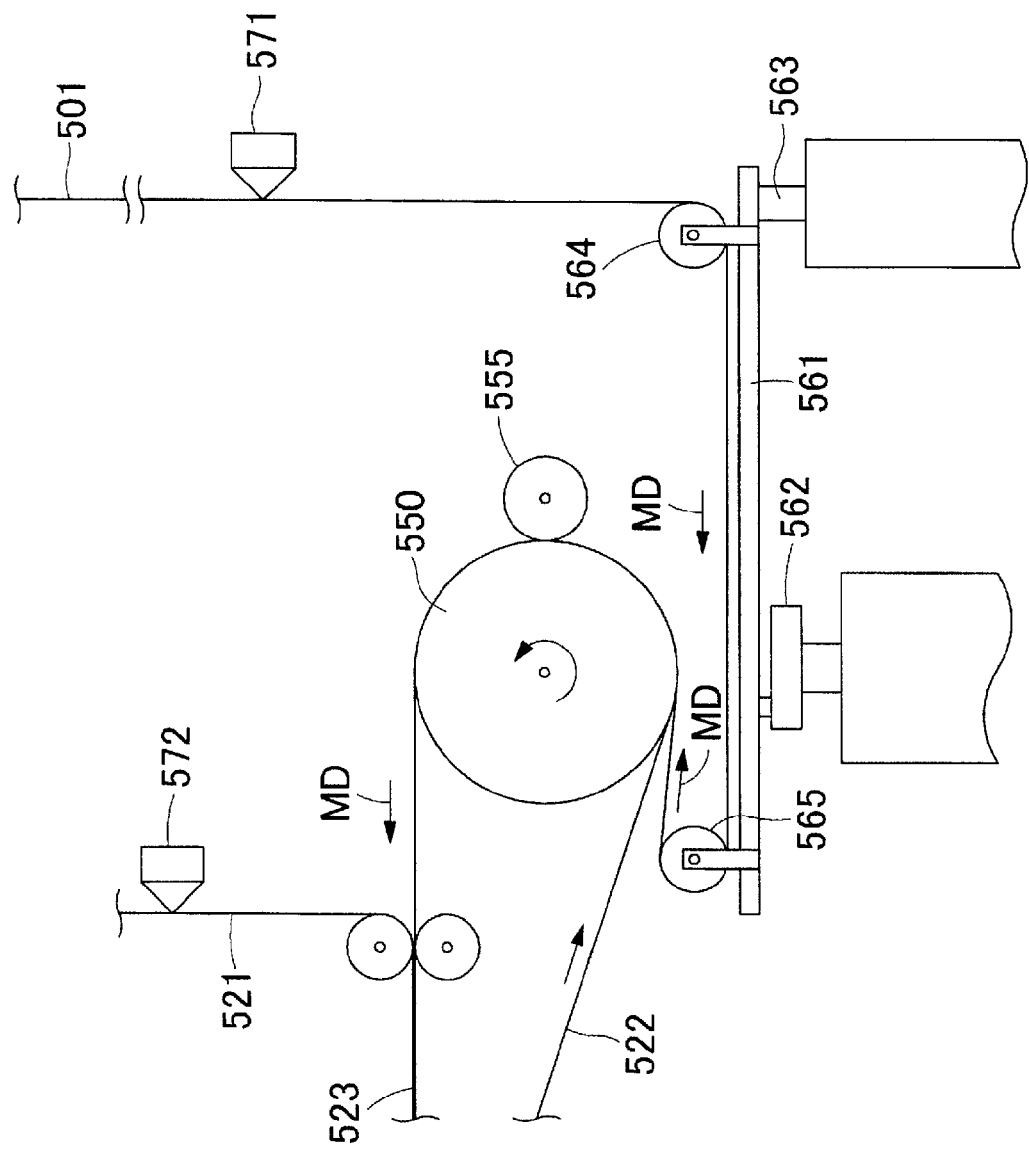
FIG. 6 is a schematic partial side view of exemplary main units used in a process for making the diaper in accordance with one or more embodiments.
Figure 7:
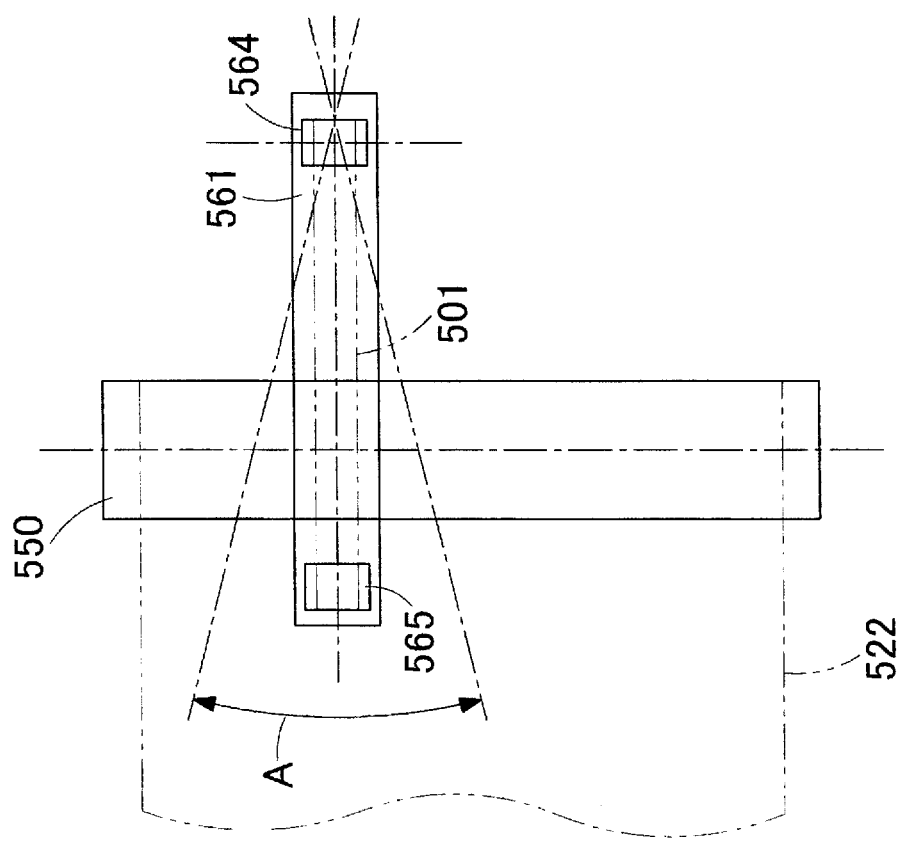
FIG. 7 is a partial overhead view of the main units in FIG. 6.

FIG. 6 is a schematic partial side view of main units used in a process for making the front panel 270 exemplarily illustrated by FIGS. 1 through 3, and FIG. 7 is a partial overhead view of these main units. Referring to FIG. 6, an elastic fibrous non-woven fabric web 501 used to form the front leg elastic band $14_F$ is continuously fed from above as viewed in FIG. 6. The elastic fibrous non-woven fabric web 501 is elastically elongated longitudinally to a desired elongation extension of its length in the relaxed state and then fed to a first coater 571. The elastic fibrous non-woven fabric web 501 is coated by the first coater 571 with hot melt adhesive (not shown). The elastic fibrous non-woven fabric web 501 coated with the adhesive is guided by guide rolls 564, 565 mounted on an oscillating arm 561 in a machine direction MD as indicated by the respective arrow(s). The elastic fibrous non-woven fabric web 501 is further put flat together, on an assemble roll 550, with a second fibrous non-woven fabric web 522 continuously fed from the left hand as viewed in FIG. 6 and bonded to the second fibrous non-woven fabric web 522 under pressure of a pressure roll 555. The second fibrous non-woven fabric web 522, and the elastic fibrous non-woven fabric web 501 bonded thereto, is further transported in the machine direction MD as indicated by the respective arrow(s). The second fibrous non-woven fabric web 522 and the elastic fibrous non-woven fabric web 501 bonded thereto join a first fibrous non-woven fabric web 521 fed from above viewed in FIG. 6 and at least the second fibrous non-woven fabric web 522 of the second fibrous non-woven fabric web 522 and the elastic fibrous non-woven fabric web 501 is bonded together with the first fibrous non-woven fabric web 521 which has been coated by a second coater 572 with hot melt adhesive (not shown). The result is a composite web 523 in which the first and second fibrous non-woven fabric webs 521, 522 sandwich therebetween the elastic fibrous non-woven fabric web 501. The oscillating arm 561 swings back and forth in a range indicated by a double headed arrow A in FIG. 7 under action of a drive 562. In FIG. 7, the elastic fibrous non-woven fabric web 501 and the second fibrous non-woven fabric web 522 are indicated by imaginary lines.

Figure 8:
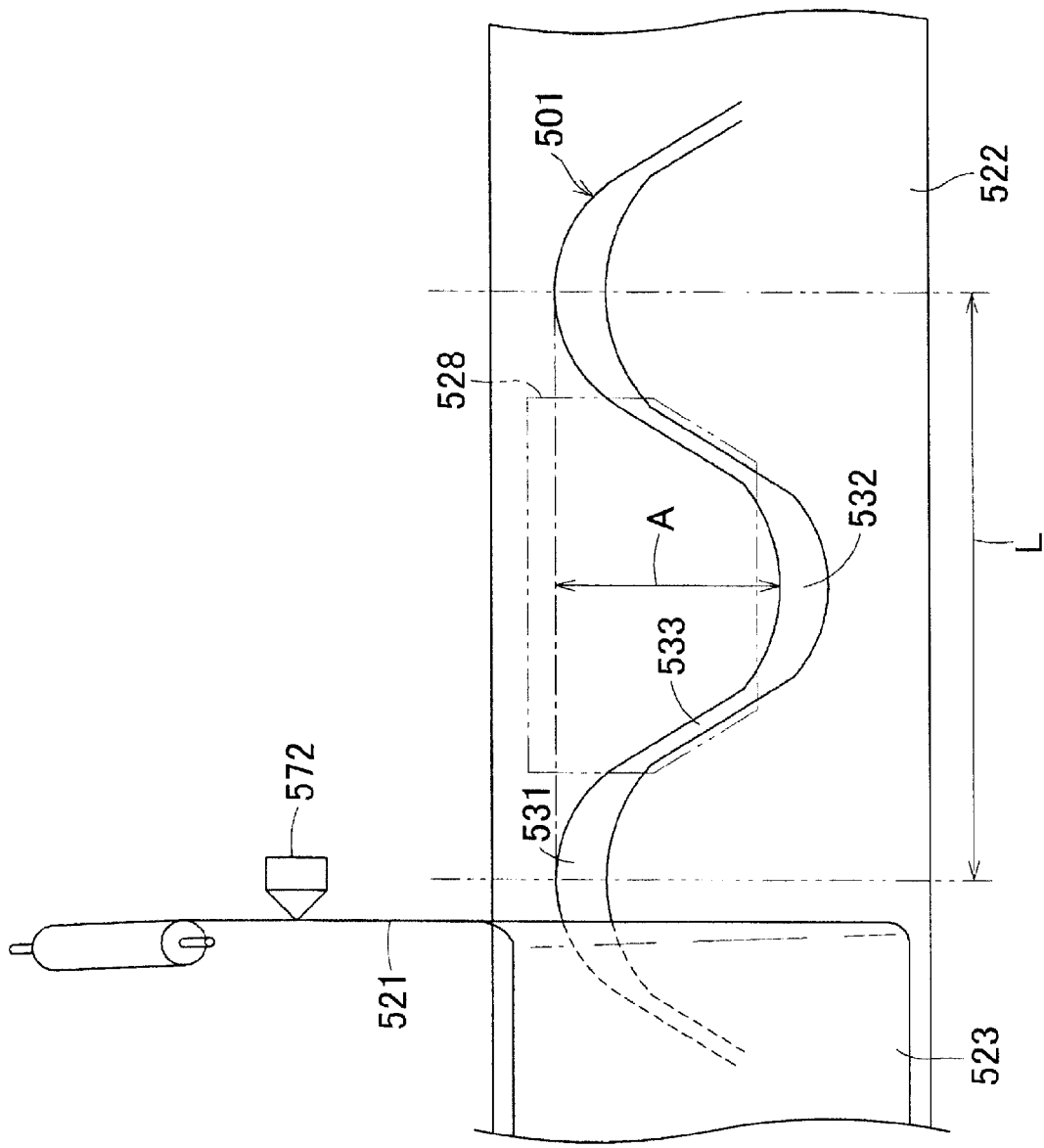
FIG. 8 is a partial plan view of a fibrous non-woven fabric web used in the process for fabricating the diaper.

FIG. 8 is a partial plan view of the second fibrous non-woven fabric web 522 to which the elastic fibrous non-woven fabric web 501 has been bonded, wherein the first fibrous non-woven fabric web 521 and the composite web 523 are also shown at the left hand of FIG. 8. An imaginary line 528 in the second fibrous non-woven fabric web 522 indicates a line along which the front panel 270 is to be cut from the composite web 523 (See FIG. 6). It should be appreciated that the front waist band $13_F$ attached to the front panel 270 is not shown for the sake of simplicity.

According to one preferred embodiment of the method of fabricating the composite web 523 using the main units and processes illustrated by FIGS. 6 and 7, a spunbonded fibrous non-woven fabric having a basis mass of 25 g/m$^2$ and a width of about 220 mm and made of polypropylene fibers is fed as the second fibrous non-woven fabric web 522 in the machine direction MD at a rate of 70 m/min. The elastic fibrous non-woven fabric web 501 is made of, for example, a spunbonded fibrous non-woven fabric including polyurethane fibers of 47% by mass and polypropylene fibers of 53% by mass and has a basis mass of 30 g/m$^2$ and a width of 80 mm in the relaxed state. The elastic fibrous non-woven fabric web 501 moves in the machine direction MD under tension caused by an elongation extension of 3 times its length in the relaxed state and is fed to the first coater 571 to be coated with hot melt adhesive at a rate of 3 g/m$^2$. The elastic fibrous non-woven fabric web 501 is further fed toward the oscillating arm 561 and then attached to the second fibrous non-woven fabric web 522 under tension. The oscillating arm 561 has its oscillation amplitude A set to 166 mm (shown in FIG. 8 as the length "A") and swings so that the second fibrous non-woven fabric web 522 is fed in the machine direction MD by 340 mm (shown in FIG. 8 as the length "L") for every operating cycle of the oscillating arm 561. The elastic fibrous non-woven fabric web 501 is guided by the oscillating arm 561 and fed, so as to describe a wave-like curve, toward and bonded to the second fibrous non-woven fabric web 522. During this step of feeding the elastic fibrous non-woven fabric web 501, oscillations of the oscillating arm 561, on the one hand, cause the width of the elastic fibrous non-woven fabric web 501 to be wide in the crests 531 and the troughs 532 of the wave-like curve. On the other hand, oscillations of the oscillating arm 561 cause the width of the elastic fibrous non-woven fabric web 501 to be narrow in an intermediate segment 533 defined between each pair of the adjacent crest and trough 531, 532 of the wave-like curve. The narrow width of the elastic fibrous non-woven fabric web 501 in such intermediate segment 533 is due to the creation of plural transversely undulating gathers (i.e., first gathers 35 in FIG. 4). Also in this step, changes of the tension occur in the elastic fibrous non-woven fabric web 501. Depending on a specific operating conditions of the equipment illustrated by FIGS. 6 and 7, in the course to bond the elastic fibrous non-woven fabric web 501 to the second fibrous non-woven fabric web 522, the width of the elastic fibrous non-woven fabric web 501 which is originally 80 mm is changed to about 32 mm in the crests 531 and the troughs 532 of the wave-like curve, reduced to the minimum about 21 mm in the respective intermediate segments 533. In the intermediate segments 533, a plurality of first gathers 35 are created as exemplarily illustrated in FIG. 4 but in the crests 531 and the troughs 532 of the wave-like curve, the elastic fibrous non-woven fabric web 501 is flat substantially free from the first gathers. As the first fibrous non-woven fabric web 521 to be put flat on the second fibrous non-woven fabric web 522, a spunbonded/melt blown/spunbonded (SMS) fibrous non-woven fabric made of polypropylene fiber having a basis mass of about 15 g/m² and a width of about 200 mm coated with hot melt adhesive at a rate of 3 g/m² is used. The composite web 523 comprising these first, second fibrous non-woven fabric webs 521, 522 and the elastic fibrous non-woven fabric web 501 is cut off in a shape as indicated by the imaginary line 528 and used as the front panel 270 as shown by FIG. 5. In the front panel 270, the inner sheet 271 defined by the first fibrous non-woven fabric web 521 is formed with the second gathers 32a comprising the crests 271a and the troughs 271b, and the outer sheet 272 defined by the second fibrous non-woven fabric web 522 is formed with the second gathers 32b comprising the crests 272a and the troughs 272b as the front leg elastic band 14$_F$ defined by the elastic fibrous non-woven fabric web 501 contracts.

Referring to FIG. 8, the elastic fibrous non-woven fabric web 501 can be put flat over a sufficiently large width upon the first and second fibrous non-woven fabric webs 521, 522 not only in the crests 531 and troughs 532 of the wave-like curve but also in the intermediate segments 533 to bond these webs one to another with hot melt adhesive coated at the coating rate only in a range of about 2 to about 10 g/m². Comparing to the case bonding rubber thread to a web in a stretched state, the coating rate of hot melt adhesive can be reduced in this manner, and in consequence, softness and comfortable texture of the article can be improved.

TABLE 1 lists various thicknesses of the span bonded/melt blown/spunbonded fibrous non-woven fabric (SMS fibrous non-woven fabric) of polypropylene having a basis mass of 15 g/m² and used as the first fibrous non-woven fabric web 521 in the processes illustrated by FIGS. 6 and 7, the spunbonded fibrous non-woven fabric (SB non-woven fibrous fabric) of polypropylene having a basis mass of 17 g/m² and used as the second fibrous non-woven fabric web 522 in these processes, and the elastic spunbonded fibrous non-woven fabric (SB fibrous non-woven fabric) having a basis mass of 30 g/m² and used as the original fabric of the elastic fibrous non-woven fabric web 501 in these processes. In addition, TABLE 1 lists the thickness of the composite web 523 illustrated by FIG. 8 comprising these webs 521, 522, 501. It should be appreciated that the thickness of the composite web 523 listed in TABLE 1 is the thickness measured in the region of the composite web 523 including the intermediate segment 533 of the elastic fibrous non-woven fabric web 501. In the intermediate segment 533, the elastic fibrous non-woven fabric web 501 is under extension, wherein the length of the elastic fibrous non-woven fabric web 501 is approximately 2.2 times longer than the length of the elastic fibrous non-woven fabric web 501 in the relaxed state, and includes a plurality of first gathers 35 as exemplarily illustrated by FIG. 4. For the thickness measurement of this region, the region including the intermediate segment 533 was cut over a length of 30 mm from the composite web 523 under tension to obtain test pieces for measurement. The thickness of such test piece left free to contract (contracted state) and the thickness of such test piece stretched until the second gathers 32a, 32b in the first and second fibrous non-woven fabric webs 521, 522 disappear (stretched state), i.e., until the elongation rate of the elastic fibrous non-woven fabric web 501 increases up to about 2.2 times with respect to the length in the relaxed state, were measured. TABLE 1 also lists the thickness of a comparative composite web obtained by making a comparative elastic fibrous non-woven fabric web in the first step, by fixing opposite ends of an original fabric having a width of 80 mm and a length of 100 mm to an appropriate jig to restrict the width from contracting at these ends, stretching the comparative elastic fibrous non-woven fabric web by about 2.2 times in the length direction, and then coating opposite surfaces of this comparative elastic fibrous non-woven fabric web under such tension with hot melt adhesive at a rate of about 3 g/m² and bonding the first and second fibrous non-woven fabric webs 521, 522 to the respective surfaces of this comparative elastic fibrous non-woven fabric web. In other words, the comparative composite web is similar to the composite web 523, except that the comparative composite web does not have gathers in its elastic fibrous non-woven fabric web, unlike first gathers 35 in the elastic fibrous non-woven fabric web 501 of the composite web 523. The thickness of the comparative elastic web in a relaxed state as well as the thickness thereof under extension by about 2.2 times were measured similarly to composite web 523, and are is listed in TABLE 1. For the thickness measurement, Automatic Compression Tester KES FB3-AUTO-A was used, wherein an area of the contact shoe was set to 2 cm², a movement rate of the contact shoe was set to 0.02 mm/sec and a contact pressure of the contact shoe was set to 0.5 g/cm².

Referring to TABLE 1, the thickness of the test piece, i.e., the thickness of the composite web 523 in the region including the intermediate segment 533 is larger than the total thickness of the first and second fibrous non-woven fabric webs 521, 522 and the elastic fibrous non-woven fabric web 501 whether it is in a contracted state or in a stretched state. The thickness of the composite web 523 is larger than the thickness of the comparative composite web whether it is in a contracted state or in a stretched state. Such measurement results indicated in TABLE 1 are believed to have been caused by the creation of the first gathers 35 in the composite web 523 as exemplarily illustrated by FIG. 4.

Figure 9:
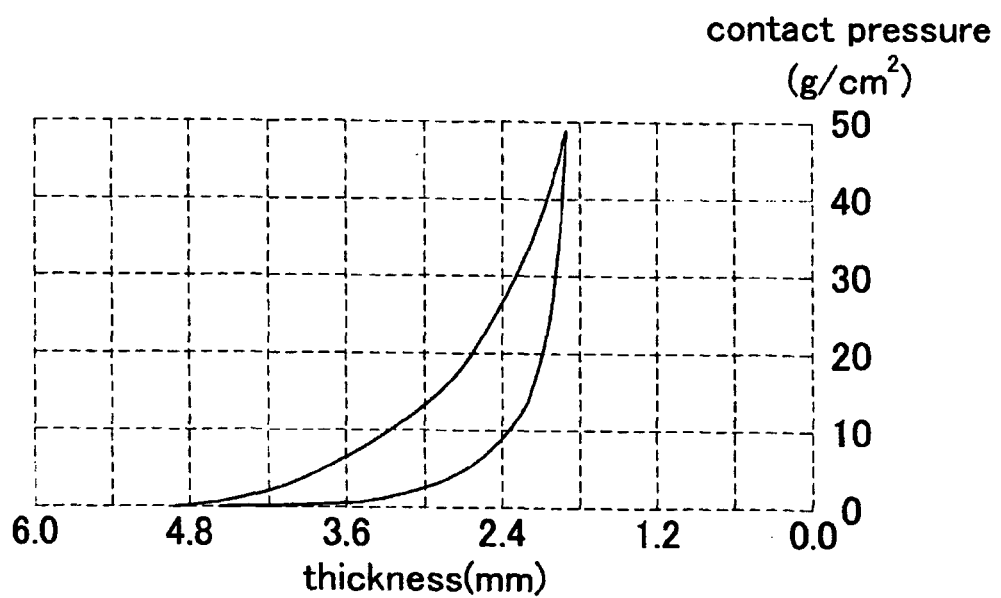
FIG. 9 is a graph showing a relationship of thickness versus compression force in a composite web in accordance with one or more embodiments.
Figure 10:
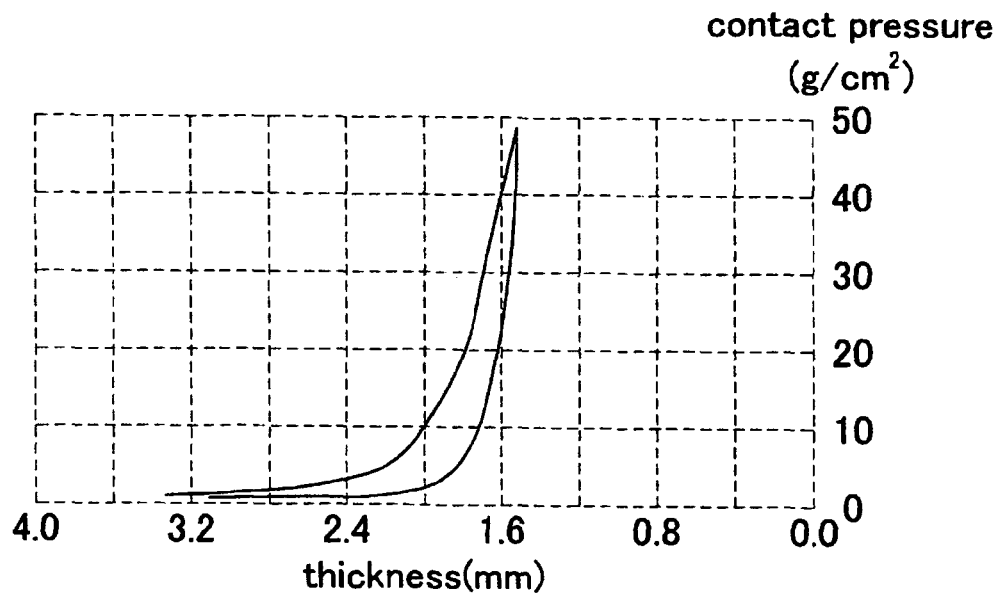
FIG. 10 is a graph showing a relation ship of thickness versus compression force in a comparative composite web.

FIGS. 9 and 10 are graphs respectively showing relationships of thickness versus compression force in the composite web 523 and in the comparative composite web shown in Table 1. In each graph the upper line shows the thickness versus compression force brought by increasing the compression force from 0 g/cm² to 50 g/cm² and the lower line shows the thickness versus compression force brought by decreasing the compression force from 50 g/cm² to 0 g/cm². In order to obtain these graphs, Automatic Compression Tester KES FB3-AUTO-A was used. The thicknesses of the composite web 523 and the comparative composite web were measured by increasing or decreasing the contact pressure of the contact shoe of the tester and were plotted as in FIGS. 9 and 10. Compared to the comparative composite web, the thickness of the composite web 523 is relatively larger and moderately changes as the contact pressure increases.

TABLE 1

| Objects to be measured | Basis mass | Thickness (mm) In non-stretched or relaxed state | Thickness (mm) In stretched state | Elongation time (s) of elastic fibrous nonwoven fabric web against the web in relaxed state | With or without gathering of elastic fibrous nonwoven fabric web |
|---|---|---|---|---|---|
| 1st fibrous nonwoven fabric (SMS nonwoven fabric) | 15 g/m² | 0.26 | — | — | — |
| 2nd fibrous nonwoven fabric (SB nonwoven fabric) | 17 g/m² | 0.26 | — | — | — |
| Original fabric of elastic fibrous nonwoven fabric web (SB nonwoven fabric) | 30 g/m² | 1.36 | — | 1 | Without |
|  |  | 1.88 in total |  |  |  |
| Composite web | — | 4.62 | 3.86 | 2.2 | With |
| Comparative composite web | — | 3.02 | 0.93 | 2.2 | Without |

To provide in the front waist elastic band 13$_F$ and/or rear waist elastic band 13$_R$ gathers that longitudinally extend along a circumferential direction of the waist-opening 11 and alternate in a width direction of the front waist elastic band 13$_F$ and/or rear waist elastic band 13$_R$, an original web destined to be the elastic bands 13$_F$, 13$_R$ can be pressed between two working tools engaged each other under heating to make gathers before bonding the elastic bands 13$_F$, 13$_R$ to fibrous non-woven fabric webs. The front leg elastic band 14$_F$ and/or rear leg elastic band 14$_R$ can also be obtained in this manner.

Although the exemplary embodiments have been described hereinabove with respect to a disposable diaper, other embodiments (not shown) are implemented in the other types of disposable wearing article, such as open-type diapers, training pants, incontinent briefs or menstruation panties etc.

The aspects of the present invention described above may be arranged in at least following items:

(i) The disposable wearing article (1) comprises:
front and rear waist regions (7, 8),
a crotch region (6) between the front and rear waist regions,
a waist-opening (11) defined by the front and rear waist regions, and
leg-openings (12) defined by the front and rear waist regions and the crotch region,
wherein a periphery of at least one of the waist-opening and the leg-openings has an elastic region (17$_F$, 17$_R$ or 15$_F$, 15$_R$) including an elastic band (13$_F$, 13$_R$ or 14$_F$, 14$_R$) formed of a first fibrous sheet which is elastically contractible in a circumferential direction (P) of the at least one of the waist-opening and the leg-openings;
the elastic band including a plurality of first gathers (35) which extend in a length direction of the elastic band along with the circumferential direction and undulate in a width direction (Q) of the elastic band.

The aspect of the present invention described in the above item (i) may provide one or more of the following advantageous effects:

(a) The undulation of the elastic band is elastically deformed as the elastic region is compressed in the thickness direction so as to keep the periphery of the at least one of the waist-opening and the leg-openings in soft and comfortably textured conditions.

Additionally, the following items may include in accordance with further aspects:

(ii) The front and rear waist regions comprise an inner sheet (271, 281) and an outer sheet (272, 282), the elastic band is sandwiched between the inner and outer sheets,
at least one of the inner and outer sheets is formed with second gathers (32) which extend transverse to the length direction of the elastic band, when said elastic band is in a contracted state.

(iii) The periphery of the leg-openings comprises at least one of a front periphery extending in the front waist region and a rear periphery extending in the rear waist region.

(iv) The elastic band has a width of at least 10 mm.

(v) The elastic band has a width in a range from 10 to 40 mm.

(vi) The first gathers of the elastic band include, in the width direction, 3 to 7 crests or troughs per unit width of 10 mm.

(vii) The first gathers of the elastic band include, in the width direction, alternating crests and troughs, and
a height of the crests is in a range of 1.2 to 3 times a thickness of the first fibrous sheet.

(viii) A basis mass of the first fibrous sheet is in a range of 20 to 100 g/m².

(ix) At least one of the inner and outer sheet is formed of a second fibrous sheet.

(x) The first and second fibrous sheets are fibrous nonwoven fabrics.

The invention claimed is:
1. A disposable wearing article, comprising:
front and rear waist regions,
a crotch region between said front and rear waist regions,
a waist-opening defined by said front and rear waist regions, and
leg-openings defined by said front and rear waist regions and said crotch region,
wherein
a periphery of at least one of said waist-opening and said leg-openings has an elastic region including an elastic band formed of a first fibrous sheet which is elastically contractible in a circumferential direction of said at least one of said waist-opening and said leg-openings,
said elastic band includes a plurality of first gathers which extend in a length direction of said elastic band along said circumferential direction and undulate in a width direction of said elastic band, the first gathers of said elastic band include crests and troughs in a thickness direction of said elastic band as viewed in a cross-section taken in the width direction of said elastic band, said front and rear waist regions comprise an inner sheet and an outer sheet, said elastic band is sandwiched between said inner and outer sheets, the crests and troughs of the elastic band are directly bonded to the inner sheet and the outer sheet by adhesive, respectively, and the inner and outer sheets are directly bonded together along both sides of the elastic band in the width direction of the elastic band.

2. The wearing article defined by claim 1, wherein
at least one of said inner and outer sheets is formed with second gathers which extend transverse to the length direction of said elastic band, when said elastic band is in a contracted state.

3. The wearing article defined by claim 1, wherein said periphery of said leg-openings comprises at least one of a front periphery extending in said front waist region and a rear periphery extending in said rear waist region.

4. The wearing article defined by claim 1, wherein said elastic band has a width of at least 10 mm.

5. The wearing article defined by claim 1, wherein said elastic band has a width in a range from 10 to 40 mm.

6. The wearing article defined by claim 1, wherein the first gathers of said elastic band include, as viewed in the cross-section taken in the width direction of said elastic band, 3 to 7 crests or troughs per unit width of 10 mm.

7. The wearing article defined by claim 1, wherein
the crests and troughs of said first gathers of said elastic band are alternatively arranged as viewed in the cross-section taken in the width direction of said elastic band, and a height of said crests as viewed in the cross-section taken in the width direction of said elastic band is in a range of 1.2 to 3 times a thickness of said first fibrous sheet.

8. The wearing article defined by claim 1, wherein
a basis mass of said first fibrous sheet is in a range of 20 to 100 g/m$^2$.

9. The wearing article defined by claim 1, wherein
at least one of said inner and outer sheets is formed of a second fibrous sheet.

10. The wearing article defined by claim 9, wherein
said first and second sheets are fibrous non-woven fabrics.

11. The wearing article defined by claim 1, wherein said elastic band further includes intermediate portions between the corresponding crests and troughs, and the intermediate portions are free of direct bonding to the inner sheet and outer sheet.

* * * * *